US006218487B1

(12) United States Patent
Van Tol

(10) Patent No.: US 6,218,487 B1
(45) Date of Patent: Apr. 17, 2001

(54) PROCESS FOR POLYMERIZING OLEFINS

(75) Inventor: Maurits F. H. Van Tol, Sittard (NL)

(73) Assignee: DSM N.V. (NL)

( * ) Notice: Subject to any disclaimer, the term of this patent is extended or adjusted under 35 U.S.C. 154(b) by 0 days.

(21) Appl. No.: 09/352,842

(22) Filed: Jul. 13, 1999

Related U.S. Application Data
(60) Provisional application No. 60/038,160, filed on Feb. 13, 1997.

(30) Foreign Application Priority Data

Jan. 14, 1997 (NL) .................................................. 1004991

(51) Int. Cl.$^7$ ........................................................ C08F 4/16
(52) U.S. Cl. ......................... 526/128; 526/160; 526/943; 526/352; 502/117; 502/152; 502/158
(58) Field of Search .................................... 526/943, 160, 526/352, 128, 123.1; 502/117, 152, 158

(56) References Cited

U.S. PATENT DOCUMENTS

| 2,992,190 | | 7/1961 | Bruce, Jr. . | |
| 3,166,547 | | 1/1965 | Loeb . | |
| 3,332,927 | | 7/1967 | Cottingham . | |
| 4,011,385 | * | 3/1977 | Wang et al. | 526/190 |
| 4,567,155 | * | 1/1986 | Tovrog et al. | 502/123 |
| 5,424,263 | * | 6/1995 | Buehler et al. | 502/116 |

FOREIGN PATENT DOCUMENTS

| 641 076 | 4/1964 | (BE) . |
| 0 780 405 A1 | 6/1997 | (EP) . |
| 1 134 740 | 4/1957 | (FR) . |
| 07 109305 | 4/1995 | (JP) . |
| WO 96/13532 | 5/1996 | (WO) . |

OTHER PUBLICATIONS

De Keijzer et al., "In search of stable lithium pentaorganyl-silicates; special role of five phenyl ligands and of ligands containing the 1,4(-1,3-butadienediyl) unit" Journal Organometallic Chem. (1997), 548(1) pp. 29-32.

Hong et al., "Synthesis and Characterization of Novel Pentavalent Silane . . . ", Organometallics (1995) vol. 14, No. 1 pp. 574-576.

Tokitoh et al, Unusual 1,2-Rearrangement of Trimethylsilyl Group in the Reaction of 2,4,6-Tris[bis(trimethylsilyl)methl]phenyllithium, Tetrahedron Letters, vol. 32, No. 18, 1991 pp. 2049-2052.

Sullivan, et al., "Gas–Phase Reactions of Cyclic Silanes", J. Am Chem. Soc., vol. 103, 1981, pp. 480-481.

* cited by examiner

Primary Examiner—David W. Wu
Assistant Examiner—R. Harlan
(74) Attorney, Agent, or Firm—Pillsbury Winthrop LLP

(57) ABSTRACT

A process for polymerizing olefins by bringing olefins into contact with a transition metal catalyst and a cocatalyst, characterized in that the cocatalyst is a compound in accordance with formula $$XR_4,$$

wherein

X is Si, Ge, Sn or Pb, and

R is hydrogen or an alkyl, aryl, arylalkyl or alkylaryl group and wherein at least one R group is not hydrogen and contains one or more halogen atoms or the cocatalyst is a compound in accordance with formula $$[XR_5]^-[Y]^+,$$

wherein X is Si, Ge, Sn or Pb,

R is hydrogen or an alkyl, aryl, arylalkyl or alkylaryl group and wherein at least one R group is hydrogen and contains one or more halogen atoms, and Y is a cation.

5 Claims, No Drawings

PROCESS FOR POLYMERIZING OLEFINS

This patent application claims priority from provisional U.S. application Ser. No. 60/038,160 filed Feb. 13, 1997.

The invention relates to a process for polymerizing olefins by bringing olefins into contact with a transition metal catalyst and a cocatalyst.

The polymerization of olefins usually requires the use of not only a transition metal catalyst, but also the use of a cocatalyst to obtain an active catalyst system.

Since the 1950s, Ziegler-Natta catalysts have been used for the polymerization of olefins. If olefin polymerizations are to proceed satisfactory with these Ziegler-Natta catalysts, it is necessary to add cocatalysts. Aluminium-containing cocatalysts such as, for example, diethylaluminium chloride, are often used in combination with Ziegler-Natta catalysts.

Recently, other types of transition metal catalysts such as, for example, metallocene catalysts have also been used for the polymerization of olefins. If olefin polymerizations using metallocene catalysts are to proceed satisfactory it is likewise necessary to use a cocatalyst. Among cocatalysts often used in combination with metallocene catalysts are aluminoxanes. An example of an aluminoxane is methylaluminoxane (MAO).

The use of aluminoxanes as a cocatalyst in the polymerization of olefins with the aid of a metallocene catalyst has the drawback that a very large excess of the aluminoxane with respect to the metallocene catalyst has to be used in order to obtain an active catalyst system. Consequently, the polyolefin produced contains a high aluminium concentration, and as a result it is often necessary for the aluminium to be washed out from the polyolefin.

It is an object of the invention to provide cocatalysts which can be used in conjunction with a transition metal catalyst for the polymerization of olefins, which do not have this drawback.

The invention relates to a cocatalyst in accordance with formula $XR_4$, wherein X is Si, Ge, Sn or Pb, R is hydrogen or an alkyl, aryl, arylalkyl or alkylaryl group and wherein at least one R group is not hydrogen and contains one or more halogen atoms, or to a cocatalyst in accordance with the formula $[XR_5]^-[Y]^+$, wherein X is Si, Ge, Sn or Pb, R is hydrogen or an alkyl, aryl, arylalkyl or alkylaryl group and wherein at least one R group is not hydrogen and contains one or more halogen atoms, and Y is a cation.

In this way an active catalyst system consisting of a transition-metal catalyst with one of the compounds according to the invention as co-catalyst is obtained which is suitable for the polymerization of olefins. If the compounds according to the invention are used as a cocatalyst for the polymerization of olefins, the amount of cocatalyst which has to be used with respect to the transition metal catalyst is much lower than when an aluminoxane is used as a cocatalyst.

Lewis acids or ion complexes are also used as cocatalysts in combination with metallocene catalysts. Examples of Lewis acids are boranes such as, for example, tris (pentafluorophenyl)borane, and examples of ion complexes are borates such as, for example, dimethylanilinium tetrakis (pentafluorophenyl)borate, triphenylcarbenium tetrakis (pentafluorophenyl)borate and trityl tetrakis(3,5-trifluoromethylphenyl)borate.

Such boron-containing cocatalysts are described, for example, in EP-A-426,637, EP-A-277,003 and EP-A-277,004.

A further advantage of the use of the compounds according to the invention as a cocatalyst in the polymerization of olefins is that using these compounds is cheaper, as a rule, than using aluminoxanes, boranes or borates.

Compounds suitable as a cocatalyst are compounds in accordance with the formula $XR_4$ and compounds in accordance with the formula $[XR_5]^-[Y]^+$. X is an atom from group 14 of the Periodic Table of the Elements and can be selected from Si, Ge, Sn and Pb. Preferably, X is Si, because Si is not toxic. Here and hereinafter, the Periodic Table of the Elements is to be understood as the periodic table shown on the inside of the cover of the Handbook of Chemistry and Physics, 70th edition, 1989/1990 (New IUPAC notation).

The R groups may be identical or different and can be selected from hydrogen and alkyl, aryl, arylalkyl or alkylaryl groups. At least one R group is not hydrogen and contains one or more halogen atoms. This implies that in a compound in accordance with the formula $XR_4$ or in accordance with the formula $[XR_5]^{-[Y]+}$ at least one halogen atom is present which does not form part of the cation Y. Preferably, the R group is a hydrocarbon group containing 1–20 carbon atoms. Examples of suitable R groups are methyl, ethyl, propyl, isopropyl, hexyl, decyl and phenyl. Two R groups may together form a bridged $R_2$ group such as, for example, a biphenyl-2,2'-diyl group and a diphenyl-2,2'-diylmethane group. These R groups may contain one or more halogen atoms.

Halogen atoms are F, Cl, Br and I. Combinations of different halogen atoms may be present in one R group or distributed over various R groups. Examples of R groups containing a halogen atom are chloromethyl, 1,2-dibromoethyl, pentafluorophenyl and octafluorobiphenyl-2, 2'-diyl. Preferably, at least 2 R groups together form a bridged aryl group. More preferably, the compound in accordance with the formula $XR_4$ or $[XR_5]^-[Y]^+$ contains octafluorobiphenyl-2,2'-diyl groups.

The cation Y is, for example, a Brönsted acid which is able to donate a proton, a cation of an alkali metal or a carbene. Examples of cations are $Li^+$, $K^+$, $Na^+$, $H^+$, triphenylcarbenium, anilinium, guanidinium, glycinium, ammonium or a substituted ammonium cation in which at most 3 hydrogen atoms have been replaced by a hydrocarbyl radical having 1–20 carbon atoms, or a substituted hydrocarbyl radical having 1–20 carbon atoms, in which 1 or more of the hydrogen atoms have been replaced by a halogen atom, phosphonium radicals, substituted phosphonium radicals, in which at most 3 hydrogen atoms have been replaced by a hydrocarbyl radical having 1–20 carbon atoms or a substituted hydrocarbyl radical having 1–20 carbon atoms, in which or more of the hydrogen atoms have been replaced by a halogen atom.

Preferably, the cation is dimethylanilinium, triphenylcarbenium or $Li^+$.

Compounds in accordance with the formula $XR_4$ which contain at least one halogen atom are disclosed, for example, by 'Cohen and Massey, J. Organometal. Chem. 10(1967) 471–481', 'Tamborski et al., J. Organometal. Chem., 4(1965) 446–454' and 'Fearon and Gilman, J. Organometal. Chem., 10 (1967) 409–419'. Compounds in accordance with the formula $[XR_5]^{-[Y]+}$ are disclosed in Angew. Chem. Int.

Ed. Engl. 1996, 35, No. 10. This publication mentions lithium (2,2'-biphenyldiyltrimethylsilicate).4THF, lithium (2,2'-biphenyldiyldimethylphenylsilicate).4THF, lithium (2,2'-biphenyldiyldimethyl-t-butylsilicate).4THF and lithium pentaphenylsilicate.4HMPA. (THF is tetrahydrofuran and HMPA is hexamethylphosphortriamide.) These compounds however, do not contain any halogen atoms and nothing is suggested regarding the possible use of these compounds as a cocatalyst in the polymerization of olefins.

The abovementioned compounds can be synthesized in accordance with synthesis methods known to the man skilled in the art.

It is also possible to use the compounds according to the invention supported on a carrier material as a cocatalyst for the polymerization of olefins. Suitable carrier materials to be mentioned are $SiO_2$, $Al_2O_3$, $MgCl_2$ and polymer particles such as polystyrene beads. These carrier materials may also be modified with, for example, silanes and/or aluminoxanes and/or aluminiumalkyls. The supported cocatalysts can be synthesized prior to the polymerization but can also be formed in situ.

Various types of transition metal catalysts can be used as a catalyst for the polymerization of olefins. Examples of such catalysts are described, for example, in U.S. Pat. No. 5,096,867, WO-A-92/00333, EP-A347,129, EP-A-344,887, EP-A-129,368, EP-A-476,671, EP-A-468,651, EP-A-416,815, EP-A-351,391, EP-A-351,392, EP-A-423,101, EP-A-503,422, EP-A-516,018, EP-A-490,256, EP-A-485,820, EP-A-376,154, DE-A-4,015,254, WO-A96/13529, EP-A-530,908, WO-A-94/11406, EP-A-672,676 and WO-A-96/23010. Transition metal catalysts containing metals from group 3 of the Periodic Table of the Elements and the lanthanides can likewise be used. Supported transition metal catalysts can also be used. Suitable carrier materials to be mentioned are $SiO_2$, $Al_2O_3$, $MgCl_2$ and polymer particles such as polystyrene beads. These carrier materials may also be modified with, for example, silanes and/or aluminoxanes and/or aluminiumalkyls.

The supported transition metal catalysts may be synthesized prior to the polymerization but may also be formed in situ.

Preference is given to the use of metallocene catalysts for the polymerization of olefins in combination with a cocatalyst according to the invention. Metallocene catalysts are characterized by the presence of one or more π-bound ligands such as, for example, cyclopentadiene (Cp) ligands or ligands related to cyclopentadiene, such as, for example, indene and fluorene, in the transition metal catalyst. More preference is given to the use of a transition metal catalyst in which the transition metal is in a reduced oxidation state, as described in WO-A-96/13529.

The polymerization of olefins, for example ethylene, propylene, butene, hexene, octene and mixtures thereof and combinations with dienes can be carried out in the presence of a transition metal catalyst and the cocatalyst according to the invention. The above-described catalyst system can equally be used for the polymerization of vinylaromatic monomers such as, for example, styrene and p-methylstyrene, for the polymerization of polar vinyl monomers such as, for example, monomers containing alcohol, amine, alkyl halide, ether, amide, imine or anhydride groups, and for the polymerization of cyclic olefins such as, for example, cyclobutene, cyclopentene, cyclohexene, cycloheptene, cyclooctene, norbornene, dimethanooctahydronaphthalene and substituted norbornenes.

The amount of cocatalyst used, based on the amount of transition metal catalyst (mol:mol), is normally 1:100–1000:1, preferably 1:5–250:1.

The polymerizations can be carried out in the manner known for this purpose, and the use of the cocatalyst according to the invention does not require any significant adaptation of these methods. The polymerizations can be carried out in suspension, solution, emulsion, gas phase or as a bulk polymerization.

If the cocatalyst is to be used in a suspension polymerization or gas phase polymerization, it is preferable for the transition metal catalyst or the cocatalyst according to the invention to be used on a carrier material. Likewise, both the catalyst and the cocatalyst can be used on a carrier material. The polymerizations are carried out at temperatures of between −50° C. and +350° C., preferably between 50° C. and 250° C. Pressures employed generally are between atmospheric pressure and 250 MPa, for bulk polymerizations more particularly between 50 and 250 MPa, for the other polymerization processes between 0.5 and 25 MPa. Dispersing agents and solvents which can be employed include, for example, substituted and unsubstituted hydrocarbons such as pentane, heptane and mixtures thereof. Aromatic, possibly perfluorinated hydrocarbons, may also be used. Equally, a monomer to be used in the polymerization can be employed as a dispersing agent.

The invention will be elucidated by means of the following not-restrictive examples.

EXAMPLES

MWD is molecular weight distribution, defined as Mw/Mn. Unless stated otherwise Mz, Mw and Mn are molecular weights determined using universal calibration procedure in SEC-DV measurements.

Example I a) Synthesis of tetra(pentafluorophenyl)silane 25 ml n-butyllithium (40.1 mmol) were added to pentafluorobromobenzene (9.9 g, 40.1 mmol) in 50 ml dry diethylether at −78° C., resulting in a solution with a light red colour. After 2 hours 1.12 ml $SiCl_4$ (9.9 mmol) was added at −78° C., the solution turning light yellow in colour followed by the formation of a white slurry. The reaction was allowed to warm slowly to room temperature. The white precipitate was separated from the solvent and dried under vacuum. The yield was 80%.

b) Addition of methyllithium to tetra (pentafluorophenyl) silane

Equimolar amounts of methyllithium and tetra (pentafluorophenyl)silane were mixed in tetrahydrofuran at −78° C. The temperature was allowed to increase to room temperature, resulting in a red-orange solution.

c) addition of triphenylchloromethyl to $(C_6F_5)_4SiCH_3^-[Li(THF)_4]^+$

A solution of triphenylchloromethyl in THF (6.60 ml, 4.29 mmol) was added to $[(C_6F_5)_4SiCH_3]^-[Li(THF)_4]^+$(3.04 g, 4.29 mmol) at −78° C., the reaction mixture became an orange colour; the ice bath was removed after 15 minutes of $Ph_3CCl$ addition. At room temperature the reaction mixture became a red-orange colour. Evaporation of the tetrahydrofuran solvent yielded a light orange coloured solid. Dry petrol (40 ml) was then added to the solid to yield a pink slurry; letting the slurry settle yielded an orange coloured petrol layer and a pink coloured precipitate the petrol was then evaporated to yield a yellow solid with a small amount of white solid present. Dry petrol (50 ml) was again added to yield a light orange pink coloured slurry; letting slurry settle yielded a light orange coloured petrol and a light yellow precipitate. The petrol was evaporated to yield a light orange coloured solid. A toluene extraction was done 2 times to separate the cation anion complex from LiCl; the evaporation of toluene yielded a light pink solid. Petrol extraction was done 2 times to extract any unreacted triphenylchloromethane.

d) Polymerisation of ethylene 0.01 mmol of the metallocene catalyst bis (cyclopentadienyl)zirconiummonohydridemonochloride (obtained from Aldrich) was mixed in 100 ml pentamethylheptane at room temperature with 0.02 mmol of the compound prepared under Ib) during 1 minute.

In a stainless steel bench rig of 1 l, 750 ml pentamethylheptane was introduced, followed by 0.4 mmol trioctylaluminium (Witco GmbH). The reactor was heated to 148° C. and the ethylene pressure was equilibrated at 20 bar overpressure (21 bar). In the next step the catalyst/cocatalyst mixture was introduced. The ethylene pressure was kept constant at 20 bars during the polymerisation. After 10 minutes the polymerization, which showed a rather constant activity prophile in time, was stopped, the polymer was removed from the reactor and the yield was determined to be 10.51 g. The polymer was analyzed by GPC. MW=51.10$^3$ g/mol, Mn=21.10$^3$ g/mol, Mz=87.10$^3$ g/mol.

Example II

The polymerisation described under example Id was repeated but now at 51° C. The yield was 4,0 g.

Example III

The polymerisation described under example Id was repeated but the polymerisation time was elongated to 60 minutes. The system remained active all the time and the polymer yield appeared to be 37.1 g.

Example IV

The polymerisation described under example Id was repeated but now at 160° C. and at a polymerisation time of 30 minutes. The polymer yield was 27.3 g. The polymer was studied by GPC. $M_n$=18.10$^3$ g/mol.

Example V

The polymerisation described under example Id was repeated but now with a polymerisation time of 10 minutes at 159° C. The polymer yield was 16.4 g. The polymer was studied by GPC. $M_n$=18.10$^3$ g/mol.

Example VI

The example Id was repeated at a temperature of 160° C. during 10 minutes with a different transition metal compound: (Cp*)C$_2$H$_4$(N(CH$_3$)$_2$)TiCl$_2$, where Cp* stands for a cyclopentadienyl ring with four methyl groups, C$_2$H$_4$ is an ethylene bridge, bridging the Cp* to a N(CH$_3$)$_2$-group. The synthesis of this organometallic compound is described in WO-A-96/13529, Example I. The polymer yield was 7.4 g. The polymer was studied using GPC. $M_w$=150.10$^3$ g/mol.

Example VII

The polymerisation described under example Id was repeated but now with the catalyst bis(2-methylindenyl) dimethyl zirconium and cocatalyst of example Ic) at a temperature of 100° C. for 15 minutes. The polymer yield was 0.5 g.

Example VIII a) Synthesis of tetra(pentafluorophenyl)germanium 14.9 ml n-butyllithium (23.9 mmol) was added to pentafluorobromobenzene (5.9 g, 23.9 mmol) in 100 ml dry diethylether at −78° C. The colour of the reaction mixture became light purple. After two hours of stirring the reaction mixture had lost its purple colour. At that point 5.98 mmol germaniumtetrachloride were added at −78° C. After about 5 minutes a white precipitate was starting to form. The solvent was separated from the white precipitate and evaporated to yield a light yellow solid which was washed two times with dry petrol (hexane mixture) followed by drying under vacuum. The yield of the product was 94%. The 13C- and 19F-NMR data showed that the tetra (pentafluorophenyl)germanium was of excellent purity.

b) Addition of methyllithium to tetra(pentafluorophenyl) germanium

Methyllithium(369 μl, 0.59 mmol) was added to (C$_6$F$_5$)$_4$Ge (535.7 mg, 0.59 mmol) in dry tetrahydrofuran (50 ml), the reaction mixture became a red colour. The reaction mixture was warmed slowly to room temperature, the reaction mixture became yellow.

c) Addition of triphenylchloromethane to [(C$_6$F$_5$)$_4$GeCH$_3$]$^-$[Li(THF)$_4$]$^+$ A solution of triphenylchloromethane (0.156 M, 59 mmol)) was added to [(C$_6$F$_5$)$_4$GeCH$_3$]$^-$[Li(THF)$_4$]$^+$ at −78° C., the reaction mixture remained yellow also at room temperature; the ice bath was removed after 15 minutes of Ph$_3$CCl addition. The tetrahydrofuran solvent was evaporated to yield a light yellow-white solid. The solid was washed 3 times with dry petrol and dried under vacuum to yield an off-white solid. Dry petrol was used to extract any unreacted Ph$_3$CCl, extraction was done 3 times; evaporation of petrol yielded a white solid.

Example IX

Polymerization of ethylene

The example Id was repeated at a temperature of 100° C. for 15 minutes, but now with the transition metal complex bis(2-methylindenyl) dimethyl zirconium, and tetra (pentafluorophenyl)germanium ((C$_6$F$_5$)$_4$Ge) (Example VIIIa) as the cocatalyst. The polymer yield was 1.9 g.

Example X

The example IX was repeated, but now with the transition metal complex bis(pentamethylcyclopentadienyl) dimethylzirconium. The polymer yield was 3.3 g.

Example XI

Synthesis of the 2H,2'H-Octafluorobiphenyl

Activated copper bronze (3.3 g, 51.9 mmol) dimethylformamide (25 ml), and 1-bromo-2,3,4,5-tetrafluorobenzene (5.0 g, 22.3 mmol) were refluxed overnight (16 hrs).

The copper was filtered off. In a next step, water was added to the filtrate and then the product was extracted with ether. The ether extract was separated using a separation funnel and dried with MgSO$_4$. The ether extract was filtered and evaporated under vacuum to yield a brown solid (yield= 40%). The solid was sublimated to yield pure white crystals (yield=34%) $^1$H NMR(C$_6$D$_6$) multiplet due to H-F coupling at 6.1 ppm.

Example XII

Synthesis of bis(octafluorobiphenyl)germanium 3.6 mmol (1.0775 g) 2H,2'H-octafluorobiphenyl was dissolved in a schlenk in 50 ml dry ether. The schlenk was cooled to −65° C. and 7.2 mmol (4.5 ml, 1.5 M) BuLi was added to the reaction mixture. This resulted in a light yellow solution. After three hours stirring at this low temperature, the reaction mixture became colourless. Now, 1.8 mmol (205 μl) GeCl$_4$ was added at −65° C. After 5 minutes stirring, the reaction mixture became cloudy. The mixture was allowed to warm-up to room temperature and after stirring overnight, the reaction mixture was a yellow-white slurry. Ether was evaporated and the resulting light yellow oil was washed two times with dry petrol to remove the ether. The result after evaporating the petrol was a white oil.

Example XIII a) Synthesis of bis(octafluorobiphenyl)silane via 2H,2'H-Octafluorobiphenyl n-BuLi (4.5 ml, 7.2 mmol) was added to 2H,2'H-octafluorobiphenyl (1.07 g, 3.6 mmol) in dry ether (20 ml) at −78° C. The reaction mixture became a light orange colour. After 2 hours $SiCl_4$(203 μl,1.79 mmol) was added. The reaction mixture became a red-purple colour. The reaction was warmed to room temperature slowly. A white precipitate (LiCl) was formed. The reaction mixture was filtered off and then the ether was evaporated to yield a white oil.

b) Synthesis of bis(octafluorobiphenyl)silane via the Grignard

Ethylmagnesiumbromide (6.8 ml, 6.8 mmol) was added to 2H,2'H-Octafluorobiphenyl (1.0 g, 3.4 mmol) in dry tetrahydrofuran (50 ml) at −78° C. The reaction was warmed to room temperature slowly. The reaction mixture became a clear yellow solution. The reaction was cooled to −78° C. The reaction mixture obtained a non-clear yellow colour. $SiCl_4$(192 μl, 1.7 mmol) was added. The reaction was warmed to reach room temperature slowly. The reaction mixture became a clear yellow colour. The reaction was warmed to room temperature slowly. Letting the reaction mixture stir for five days yielded a clear light yellow solution. Evaporation of tetrahyrofuran solvent yielded a white solid. The white solid was washed one time with petrol and dried under vacuum. ClMgBr salt was separated from the white solid using dichloromethane.

c) Addition of methyllithium to bis(octafluorobiphenyl)silane

Methyllithium (553 μl, 0.819 mmol) was added to bis(octafluorobiphenyl)silane (507.7 mg, 0.819 mmol) in dry tetrahydrofuran (40 ml) at −78° C. The reaction mixture was warmed slowly to room temperature, no colour change was observed.

d) Addition of triphenylchloromethane to $[Si(Cl_2F_8)_2CH_3]^{31}$ $[Li.THF_4]^+$ A solution of triphenylchloromethane (1.28 ml, 0.619 mmol) was added to $[Si(C_{12}F_8)_2CH_3]^-[LiTHF_4]^-$ (393.1 mg, 0.619 mmol) in dry tetrahydrofuran (30 ml) at −78° C. The ice bath was removed 15 minutes after $Ph_3CCl$ addition. At room temperature the reaction mixture became a brown-yellow colour. Evaporation of the tetrahydrofuran solvent yielded a light brown which was washed 2 times with dry petrol and dried under vacuum to yield a red-pink solid (yield=97%).

What is claimed is:

1. Process for polymerizing olefins by bringing olefins into contact with a transition metal catalyst and a cocatalyst, wherein the cocatalyst is a compound in accordance with formula $XR_4$, wherein X is Si, Ge, Sn or Pb, and R is hydrogen, an alkyl, aryl, arylalkyl or alkylaryl group and wherein at least one R group is not hydrogen and contains one or more halogen atoms.

2. Process for polymerizing olefins by bringing olefins into contact, under polymerization conditions, with a transition metal catalyst and a cocatalyst, wherein the cocatalyst is a compound in accordance with formula $$[XR_5]^-[Y]^+,$$

wherein

X is Si, Ge, Sn or Pb,

R is hydrogen, an alkyl, aryl, arylalkyl or alkylaryl group and wherein at least one R group is hydrogen and contains one or more halogen atoms, and Y is a cation.

3. Process according to either claim 1 or 2, wherein the transition metal catalyst is a metallocene catalyst.

4. Process according to claim 3, wherein the transition metal catalyst contains a transition metal which is in a reduced oxidation state.

5. Process according to either claim 1 or 2, wherein at least 2 R groups together form a bridged aryl group.

* * * * *